United States Patent [19]

Kimura et al.

[11] 4,263,326
[45] Apr. 21, 1981

[54] ANTIMICROBIAL COMPOSITIONS CONTAINING AN OCTYLPHENONE

[75] Inventors: Yukichi Kimura, Narashino; Takeshi Kanamori, Chiba; Tomonori Sakamoto, Kamagaya, all of Japan

[73] Assignee: The Lion Dentrifice Co. Ltd., Tokyo, Japan

[21] Appl. No.: 90,043

[22] Filed: Oct. 31, 1979

[30] Foreign Application Priority Data

Nov. 17, 1978 [JP] Japan .................................. 53-141927

[51] Int. Cl.$^3$ ............................................. A01N 35/00
[52] U.S. Cl. ..................................................... 424/331
[58] Field of Search ......................... 424/331; 260/592

[56] References Cited

U.S. PATENT DOCUMENTS 3,686,319  8/1972  Lafon .................................... 424/331

OTHER PUBLICATIONS

Chem. Abst. 77, 47,011(j), (1972)-Ueno.

Chem. Abst. 79, 64557(a), (1973)-Ueno et al.

*Primary Examiner*—Douglas W. Robinson
*Attorney, Agent, or Firm*—Toren, McGeady and Stanger

[57] ABSTRACT

A novel antimicrobial agent is proposed which is effective for preventing growth of microorganisms belonging not only to bacteria but also to Eumycetes in foodstuffs, cosmetics, medicines and the like. The inventive antimicrobial agent contains 2',6'-dihydroxy-9-(2,5-dihydroxyphenyl) octylphenone as the effective ingredient thereof and its effectiveness is exhibited in a concentration level of from 0.0001 to 1% by weight as the phenone compound in the foodstuff etc. Different from conventional synthetic antimicrobial agents used in foodstuffs and the like, the inventive antimicrobial agent is absolutely free from the problem of safety when taken into human body in any large amounts since the phenone compound as the effective ingredient thereof is a product of natural origin and can be obtained from mace by extraction.

4 Claims, 1 Drawing Figure

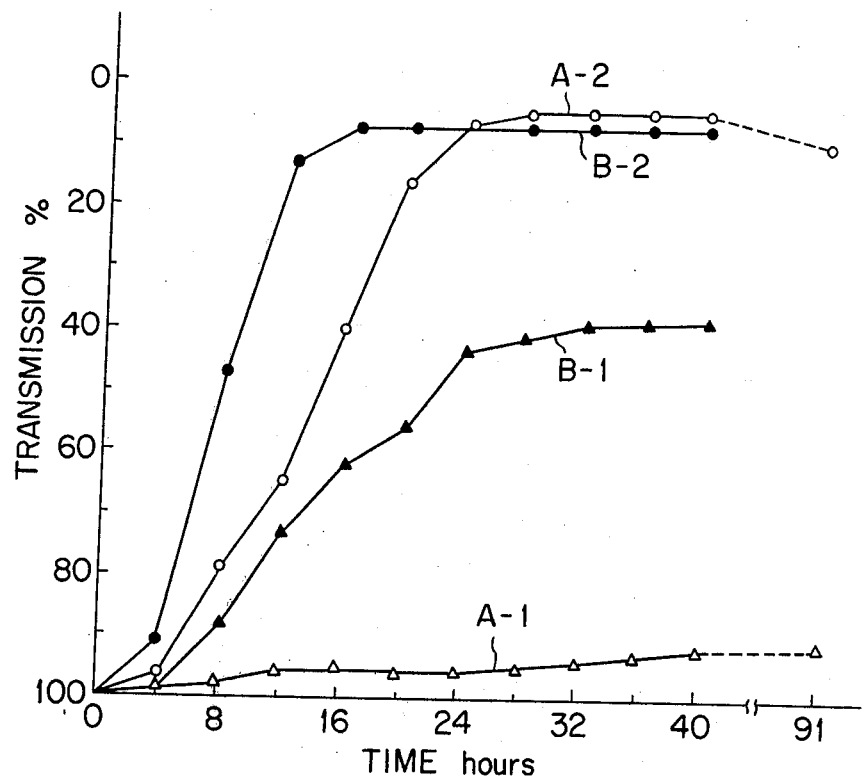

ANTIMICROBIAL COMPOSITIONS CONTAINING AN OCTYLPHENONE

BACKGROUND OF THE INVENTION

The present invention relates to a novel antimicrobial agent, i.e. an antibacterial and antifungal agent, containing 2',6'-dihydroxy-9-(2,5-dihydroxyphenyl)octylphenone as an effective ingredient thereof and also to a method for preventing growth or multiplication of microorganisms in foodstuffs, cosmetics, medicines and the like. The inventive antimicrobial agent is particularly effective as an antibacterial agent or as an antifungal agent when incorporated into various kinds of foodstuffs, especially, containing little or no fats or oils, such as fruit wines or ratafias, jams, catchups, processed fish pastes, soy sauces and the like as well as various kinds of cosmetics and medicines.

Many kinds of antimicrobial or antiseptic agents are hitherto known and used in order to prevent growth of putrefactive bacteria and fungi in the above named foodstuffs, cosmetics and medicines including Parabens (alkyl ethers of p-hydroxybenzoic acid, products of Washine Chemical Corp.), benzoic acid, sorbic acid and other kinds of synthetic organic compounds. It is, however, a recent trend that the use of an antimicrobial agent of natural origin is recommended from the standpoint of higher safety than with synthetic ones provided that it has a satisfactorily high antibacterial and antifungal effects even by use of a small amount thereof.

In relation to the increasing demand for the antimicrobial agents of natural origin as described above, there have been published numbers of papers dealing with the antimicrobial effect of various kinds of spices and herbs or, in particular, the essential oils extracted therefrom. The problem in the use of spices and herbs or essential oils thereof as an antimicrobial agent, in particular, in foodstuffs is that the taste and flavor of the foodstuff are detrimentally affected by the too strong spiciness thereof since they must be added in an amount much larger than used in ordinary cooking in order to obtain sufficient antimicrobial effect.

Such an undesirable influence is similarly unavoidable in the use of spices and herbs in cosmetic materials and medicines because the very delicate balance of perfumes in cosmetics is fatally destroyed by the addition so large amounts of them and medicines are imparted with a strange smell which may adversely affect the patient psychologically.

SUMMARY OF THE INVENTION

The inventors have conducted extensive investigations to develop an antimicrobial agent of natural origin which is very efficient for preventing growth of various kinds of microorganisms such as bacteria and fungi in foodstuffs, cosmetics and medicines even with a so low level of amounts of addition that the taste and flavor or fragrance of foodstuffs, cosmetics and the like are absolutely not influenced.

The inventive antimicrobial agent contains 2',6'-dihydroxy-9-(2,5-dihydroxyphenyl)octylphenone as an effective ingredient thereof, which phenone compound can be obtained from an extract of mace.

The method of the invention for preventing growth of microorganisms in foodstuffs, cosmetics, medicines and the like comprises admixing said foodstuffs, cosmetics, medicines and the like with the above mentioned antimicrobial agent in an amount of at least 0.0001% by weight as the phenone compound.

BRIEF DESCRIPTION OF THE DRAWING

Curves in the FIGURE are to illustrate the antimicrobial effect of a mace extract against Acinetobacter anitratus as measured by the bioscanner method, of which Curves A-1 and B-1 are for the wild stock and the cultured stock in tripticase soy broth culture media admixed with 0.0075% by weight of the extract, respectively, and Curves A-2 and B-2 are for the control tests with the wild stock and the cultured stock without the addition of the extract, respectively.

DETAILED DESCRIPTION OF THE PREFERRED EMBODIMENTS

The effective ingredient in the inventive antimicrobial agent is 2',6'-dihydroxy-9-(2,5-dihydroxyphenyl)octylphenone which is a compound expressed by the structural formula

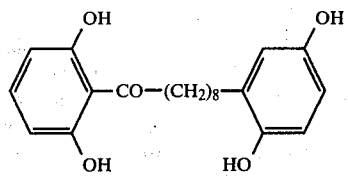

obtained as white or slightly yellowish crystals of a needle-like or plate-like form melting at 123.5° to 124° C. This compound is tasteless, odorless, non-irritant and physiologically inactive with the value of $LD_{50}$ of at least 2000 mg/kg when orally administered to rats.

The above phenone compound may be prepared synthetically but most conveniently obtained from the extract of mace with a suitable organic solvent.

Thus, for example, powdered mace per se or an oleoresin obtained by the extraction of mace with a polar organic solvent such as lower alcohols, e.g. ethyl alcohol, ethyl acetate, acetone, propylene glycol, glycerine and the like is washed or extracted with a non-polar organic solvent such as petroleum ether, ligroin, n-hexane, cyclohexane, carbon tetrachloride, chloroform, dicholormethane, 1,2-dichloroethane, toluene, benzene and the like to remove any odorous constituents and the residue is further extracted with ethyl alcohol of 60 to 90% concentration. In this case, it is recommended that the residue is first admixed with ethyl alcohol of a concentration of 95% or higher followed by dilution with water to a concentration of 60 to 90%. The extract solution is further admixed with water to give a concentration of ethyl alcohol in the range from 20 to 40% so that a solid matter precipitates. This precipitated material may be used as such in formulating the antimicrobial agent of the invention since this material contains the phenone compound in an amount of 5 to 50% by weight.

When a higher purity is desired for the phenone compound, the precipitated material is subjected to purification by the techniques of column chromatography. Thus, the precipitated material is adsorbed on a bed of an adsorbent such as silica gel and eluted out in two steps with a 9:1 mixed solvent of chloroform and acetone and then with acetone as the development solvents in the first step and with a 8:1:1 mixed solvent of chloroform, acetone and n-hexane and then with acetone as the development solvents in the second step. The solvents in the pertinent eluate fractions are evaporated to dryness, for instance, by freeze-drying and the remaining solid material is subjected to extraction with acetone and n-hexane followed by chilling of the extract solution to precipitate a crystalline material which is further purified by recrystallization from benzene to the final product.

Alternatively, a residue of mace from the extraction of essential oil may be used as the starting material in two ways. Firstly, the starting residue is extracted with ethyl alcohol of 60 to 90% concentration and the extract solution is diluted with water to give a concentration of ethyl alcohol in the range from 20 to 40% to precipitate a solid material which is subjected to the column chromatographic purification as described above. Secondly, the extract solution with ethyl alcohol of 60 to 90% concentration is evaporated to dryness to give a solid material which is then washed with hot water followed by the column chromatographic purification as described above.

As is suggested before, it is not always necessary to use the phenone compound purified by the troublesome column chromatography but, in most cases, substantially the same and satisfactory antimicrobial effect can be obtained by use of the above described precipitated material from the ethyl alcohol extract or the dried residue of the extract provided that the content of the phenone compound in the antisepticized foodstuffs etc. is at the same level in consideration of the concentration of the phenone compound in the precipitated material or the dried residue amounting to 50% by weight or higher.

The antimicrobial agent of the present invention can be used for effectively preventing growth or multiplication of various microorganisms in foodstuffs, in particular, containing little or no fats and oil such as soy sauce, soft drinks, e.g. carbonated beverages and fruit juices, alcoholic beverages, ratafias, catchups, jams, processed fish pastes and the like and cosmetics including hair care products, skin care products, oral care products and the like as well as medicines, especially, containing sufficient amounts, say, 10% by weight or more, of water to permit the growth of microorganisms.

The amount of the inventive antimicrobial agent to be added to the base materials such as foodstuffs, cosmetics, medicines and the like depends on various factors but it is usually within the range from 0.0001 to 1% or, preferably, from 0.002 to 0.5% by weight based on the amount of the base material calculated as the concentration of the phenone compound. It is of course that smaller amounts than above cannot give sufficient antimicrobial effect while larger amounts than 1% by weight give no particular additional advantages in increasing the antimicrobial effect though with no undesirable effect excepting the economical disadvantages.

2′,6′-dihydroxy-9-(2,5-dihydroxyphenyl)octylphenone as the effective ingredient of the inventive antimicrobial agent is effective for preventing growth not only of bacteria but also of microorganisms belonging to Eumycetes and the antimicrobial effect of the phenone compound is particularly remarkable against gram-positive bacteria in comparison with conventional antimicrobial agents such as Parabens, benzoic acid, sorbic acid and the like even with a smaller amount of addition. For example, the antimicrobial effect of the phenone compound against Bacillus subtilis is as good as that of sorbic acid even when the concentration of the phenone compound is only one hundredth of that of sorbic acid. Thus, growth or multiplication of Bacillus subtilis in a tripticase soy broth culture medium is effectively prevented for as long as 7.5 hours or longer by the addition of 0.002% by weight of the phenone compound while sorbic acid can give an antimicrobial effect against Bacillus subtilis lasting only about 4.5 hours when added in an amount of 0.2% by weight, which concentration being the maximum permissible level in foodstuffs under the regulation of Japanese Foodstuff Law in view of safety.

The above described remarkable antimicrobial effect of the phenone compound taken together with the very high value of the $LD_{50}$ of 2000 mg/kg for rats brings about absolutely no problem of safety in the use of the inventive antimicrobial agent. Moreover, the inventive antimicrobial agent can be added to foodstuffs and the like in any large amounts because the phenone compound is colorless, tasteless, odorless and non-irritant so that the foodstuff with addition of the inventive antimicrobial agent do not undergo any changes in their color, taste and flavor. Further, there is no danger of adverse effect on the delicate balance of perfumes in cosmetics by the use of the inventive antimicrobial agent are free from any limitations in formulation and administration as without the addition of an antimicrobial agent.

In the following, examples are given to illustrate the effectiveness of the inventive antimicrobial agent containing 2′,6′-dihydroxy-9-(2,5-dihydroxyphenyl)octylphenone as the effective ingredient thereof both in culture tests and in the actual use in foodstuffs and cosmetics.

EXAMPLE 1

Tripticase soy broth culture media were prepared by admixing 2′,6′-dihydroxy-9-(2,5-dihydroxyphenyl)octylphenone in six different levels of concentration ranging from 0.002% to 0.02% by weight and Bacillus subtilis as a typical species of gram-positive bacteria was cultured in the media at 37° C. For comparative purpose, three more culture media were prepared without addition of an antimicrobial agnet or with addition of 2% by weight of ethyl alcohol or 0.2% by weight of sorbic acid instead of the phenone compound and Bacillus subtilis was cultured therein similarly.

The results of the tests summarized in Table 1 below indicate the maximum time of duration in which the growth of Bacillus subtilis could be effectively prevented in respective culture media. As is clear from the results, the phenone compound in a concentration of 0.002% is more effective than sorbic acid in a concentration of 0.2% which is the maximum permissible concentration in foodstuffs according to the regulation of the Japanese Foodstuff Law.

TABLE 1

| Antimicrobial agent | Concentration in culture medium | Time of growth prevention, hours | | | | | | | | |
|---|---|---|---|---|---|---|---|---|---|---|
| | | 3.5 | 4.5 | 7.5 | 12 | 27 | 74 | 89 | 100 | 108 |
| 2′,6′-Dihydroxy-9-(2,5-dihydroxyphenyl)octyl phenone | 0.02% | − | − | − | − | − | − | − | − | − |
| | 0.016% | − | − | − | − | − | − | − | − | − |
| | 0.012% | − | − | − | − | − | − | + | + | + |
| | 0.008% | − | − | − | − | − | + | + | + | + |
| | 0.004% | − | − | − | − | + | + | + | + | + |

TABLE 1-continued

| Anti-microbial agent | Concentration in culture medium | Time of growth prevention, hours | | | | | | | | |
|---|---|---|---|---|---|---|---|---|---|---|
| | | 3.5 | 4.5 | 7.5 | 12 | 27 | 74 | 89 | 100 | 108 |
| Ethyl alcohol | 0.002% 2% | − − | − + | − + | + + | + + | + + | + + | + + | + + |
| Sorbic acid | 0.2% | − | − | + | + | + | + | + | + | + |
| None | — | + | + | + | + | + | + | + | + | |

EXAMPLE 2

Dried extract powder was prepared by extracting powder of mace with 95% ethyl alcohol followed by drying up of the extract solution into a powder which was washed with hot water at about 90° C. The extract powder thus obtained contained about 20% by weight of 2′,6′-dihydroxy-9-(2,5-dihydroxyphenyl)octylphenone.

The antimicrobial effectiveness of this extract powder was examined against growth of the wild stock and the cultured stock of Acinetobacter anitratus, a kind of gram-negative bacteria, cultured at 37° C. in tripticase soy broth culture media without or with addition of 0.0075% by weight of the extract powder and the growth of the bacteria was examined by the bioscanner method to give the results as illustrated in the FIGURE annexed. Curves A-1 and B-1 in the FIGURE are for the wild stock and the cultured stock in the culture media with addition of the extract powder, respectively, and Curves A-2 and B-2 are for the wild stock and the cultured stock in the culture media without addition of the extract powder, respectively.

As is clear from the FIGURE, the inventive antimicrobial agent is effective also for preventing growth of gram-negative bacteria.

EXAMPLE 3

The antifungal effect of the extract powder prepared in Example 2 was examined by adding it into potato-dextrose agar culture media in an amount of 0.2% by weight in which Aspergillus niger or Penicillium crysogenum were cultured at 28° C. For comparison, similar culture tests of the fungi were undertaken with the culture media in which no antimicrobial agent was added or 5% by weight of ethyl alcohol was added instead of the extract powder.

The results are summarized in Table 2 below, in which the marks "±" are for the cases where the growth of the molds was difficultly recognized, the marks "+" are for the cases where the growth of the molds could be recognized only of the hyphae though to a small extent, the mark "++" are for the cases where the growth could be recognized only of the hyphae to a considerable extent, and the marks "+++" and "++++" are for the cases where spores were formed.

As is clear from the results in the table, the extract powder containing the phenone compound is effective also for preventing growth of microorganisms belonging to Eumycetes.

TABLE 2

| Agent added | Fungus | | | |
|---|---|---|---|---|
| | Aspergillus niger | | Penicillium crysogenum | |
| | Days Cultured | | | |
| | 10 | 18 | 10 | 18 |
| Extract powder of mace, 0.2% | + | + | ± | ± |
| Ethyl alcohol, 5% | ++ | ++ | ± | ++ |
| None | +++ | ++++ | +++ | ++++ |

EXAMPLE 4

Kamaboko, which is a kind of boiled fish paste and a traditional Japanese food, was prepared by the following formulation.

| White fish meat, ground | 250 g |
|---|---|
| Cooking salt | 8.5 g |
| Monosodium glutaminate | 2 g |
| Sugar | 8 g |
| Potato Starch | 15 g |
| Water | 10 g |
| Extract powder of mace (prepared in the same manner as in Example 2 but containing about 40% by weight of the phenone compound) | 0.6 g |

The above given ingredients were kneaded uniformly in a usual manner and processed into kamaboko. For comparison, similar kamaboko was prepared in the same manner except that the extract powder of mace was replaced with an equal amount of sorbic acid.

The preservation test of these kamabokos at 37° C. indicated that the sample with the addition of the extract powder of mace was preservable without the appearance of clamminess over a period about twice as long as the sample with the addition of sorbic acid.

EXAMPLE 5

Vienna sausages were prepared by the following formulation.

| Lean of pork | 70 g |
|---|---|
| Fatty Pork | 30 g |
| Water | 25 g |
| Sugar | 1.0 g |
| Monosodium glutaminate | 0.2 g |
| Onion | 3.0 g |
| Disodium phosphate | 0.1 g |
| Pepper | 0.3 g |
| Sage | 0.1 g |
| Coriander | 0.1 g |
| Mace | 0.05 g |
| Extract powder of mace (prepared in the same manner as in Example 2 but containing about 35% by weight of the phenone compound) | 0.78 g |

The above given ingredients were kneaded uniformly in a usual manner, put into man-made casings and processed into sausages. For comparison, similar sausages were prepared by the same formulation as above except that the extract powder was replaced with 0.2% of sorbic acid. The preservability of the sausages with the addition of the extract powder was much better than that of the sorbic acid-admixed sausages as evidenced in the preservation test at 25° C. over 3 months.

EXAMPLE 6

A hair care product was prepared by the following formulation.

| | |
|---|---|
| Polyoxyethylene-polyoxypropylene monobutyl | 35 g |
| Ethyl alcohol | 25 g |
| Glycerine | 2 g |
| Water | 10 g |
| Perfume | 0.1 g |
| 2',6'-dihydroxy-9-(2,5-dihydroxyphenyl)octylphenone | 0.3 g |

The above given ingredients were blended in a usual manner into a hair care product. For comparison, a similar hair care product was prepared by the same formulation as above except that the phenone compound was replaced by a combination of 0.2 g of Ethyl Paraben and 0.1 g of Butyl Paraben. These products had no problems in their quality by the addition of the phenone compound or the Parabens and the preservability of the quality was about the same for the product admixed with the phenone compound and for the Paraben-admixed product.

What is claimed is:

1. An antimicrobial agent for preventing growth of microorganisms in foodstuffs, cosmetics, and medicines, which comprises a microbicidal effective amount of 2',6'-dihydroxy-9-(2,5-dihydroxyphenyl)octylphenone and an inert carrier.

2. A method for preventing growth of microorganisms in foodstuffs, cosmetics, and medicines, which comprises admixing the foodstuff, cosmetic, or medicine with a microbicidal effective amount of 2',6'-dihydroxy-9-(2,5-dihydroxyphenyl)octylphenone.

3. The method as claimed in claim 2 wherein the amount of the antimicrobial agent is in the range from 0.0001 to 1% by weight as the 2',6'-dihydroxy-9-(2,5-dihydroxyphenyl)octylphenone based on the amount of the foodstuff, cosmetic or medicine.

4. In a foodstuff, cosmetic, or medicine, containing a compound for preventing the growth or multiplication of microorganisms therein, the improvement wherein said compound is 2',6'-dihydroxy-9-(2,5-dihydroxyphenyl)octylphenone in a microbicidal effective amount.

* * * * *